United States Patent [19]

Ilsink

[11] Patent Number: Plant 6,698

[45] Date of Patent: Mar. 28, 1989

[54] ROSE PLANT INTERONLY

[75] Inventor: Peter Ilsink, Broekweg, Netherlands

[73] Assignee: Jackson & Perkins Company, Medford, Oreg.

[21] Appl. No.: 105,657

[22] Filed: Oct. 6, 1987

[51] Int. Cl.[4] ..... A01H 5/00

[52] U.S. Cl. ..... Plt./20

[58] Field of Search ..... Plt./20

*Primary Examiner*—Robert E. Bagwill

*Attorney, Agent, or Firm*—Majestic, Gallagher, Parsons & Siebert

[57] ABSTRACT

A rose variety of the hybrid tea class is provided having bright red flowers held on long stems that do not blue when cut, and high flower production particularly useful in greenhouse production.

1 Drawing Sheet

SUMMARY OF THE INVENTION

The present invention relates to a new and distinct variety of rose plant of the hybrid tea class, which was originated by me by crossing an unnamed seedling with an unnamed seedling.

The primary objective of this breeding was to produce a new rose variety of the hybrid tea class displaying bright red flowers with long cutting stems for greenhose production and high yield potential. This objective was substantially achieved, along with other desirable improvements, as evidenced by the following unique combination of characteristics which are outstanding in the new variety and which distinguish it from its parents as well as from all other varieties of which I am aware. For example, this new rose variety has:

1. Bright red (non-blueing) flowers;
2. Long cutting stems;
3. High cut flower production;
4. Presence of glands on appendaged stipules;
5. Petioles have prickles on the underside and are edged with glands.

Asexual reproduction of this new variety by cuttings, as performed at Wasco, Calif., shows that the foregoing characteristics and distinctions come true to form and are established and transmitted through succeeding propagation.

DESCRIPTION OF THE DRAWING

The accompanying illustration shows typical specimens of the vegetative growth and flowers of this new variety in different stages of development, depicted in color as nearly true as it is reasonably possible to make the same in a color illustration of this character.

DETAILED DESCRIPTION OF THE INVENTION

The following is a detailed description of my new rose cultivar, which has been denominated "Interonly". Color terminology is in accordance with The Royal Horticultural Society Colour Chart except where an ordinary dictionary significance for the color is apparent.

Observations of the buds and flowers were made from specimens grown in a greenhouse at Irvine, Calif. during July, 1987.

Flower

The blooming habit is continuous. The bud size is one and one-half inch when the petals start to unfurl. The bud form is long, pointed ovoid. The bud color when sepals first divide is near Red Group 44A; when half blown, the upper side of petals is near Red Group 44A and the lower side of petals is near Red Group 45A. The sepals have a color near Green Group 138B. The surface texture is covered with fine hairs. There are three appendaged sepals which are normally to heavily appendaged, and are edged with glands. Two unappendaged sepals have a hairy edge. The receptacle color is near Green Group 143C with a funnel shape, medium size and a smooth surface. The peduncle is medium, and has a smooth surface with a few small soft prickles. Peduncle color is medium green and the penduncle is stiff and erect.

Bloom

Bloom size is medium, with an average open size of three and one-half to four inches, borne singly. The stems are long and strong. The form when first open is high center. This form then flattens and the outer petals curl back, quill fashion. Under normal conditions there are 35 to 40 petals. The upper side of petals is near Red Group 44A, and the reverse side of the petals is near Red Group 45D. The base of petals has a small yellow half moon at the point of attachment to the peduncle with the major color being near Red Group 44A. There are no variegations except for occasional white streaks on the outside or very inside petals. The general tonality at the end of the first day shows no change in color. At the end of the third day, there is still no change in color.

The fragrance is slight. The petal texture is thick, of round shape, with the tips being slightly recurved and the edges slightly quilled.

The arrangement is imbricated with few petaloids in the center. The blooms drop off cleanly, and last on the plant or as a cut flower for a long period.

Reproductive Parts

The anthers are medium and many, of reddish borwn color and arranged regularly around the styles and mixed with a few petaloids. The filaments are reddish brown with a yellow base at the point of attachment to the peduncle, the pollen is gold yellow, the styles are reddish, and the stigmas are greenish white.

Plant

A vigorous upright bush.

Foliage

Medium size, normal in quantity. The new foliage is reddish green, and the old foliage is dark green. Normal mid-stem leaves have five leaflets.

The leaflets are of an oval pointed shape, are leathery and smooth in texture, and have a serrated edge. The serration is single and small. Petiole rachis is green, and has a smooth underside with prickles. The upper side is edged with glands. Stipules are medium and bearded. The foliage is susceptible to mildew under normal growing conditions at Irvine, Calif.

Wood

New wood is light green, with a smooth bark. Old wood is green with a smooth bark.

Prickles

There are an ordinary number of prickles on main canes from the base and on laterals from the main canes. The form is medium and straight. Color when young is red.

Small Prickles

There are no small prickles on the main stalks or on the laterals.

Additional Distinguishing Traits

This novel rose plant is an excellent greenhouse cut flower. Its outstanding feature is the very clear bright flower color. The flower holds its red color extremely well when cut and displayed in a vase and does not blue.

Parentage

The seed parent was an unnamed seedling. The pollen parent was also an unnamed seedling.

Classification

Botanical is rosa hybrid. Commercial is the hybrid tea.

I claim:

1. A new and distinct variety of rose plant of the hybrid tea class substantially as herein shown and described, characterized particularly as to novelty by bright red flowers that do not blue when cut on long stems, by cut flower production, presence of glands and prickles on the leaf petioles, and presence of glands on the appended stipules.

* * * * *

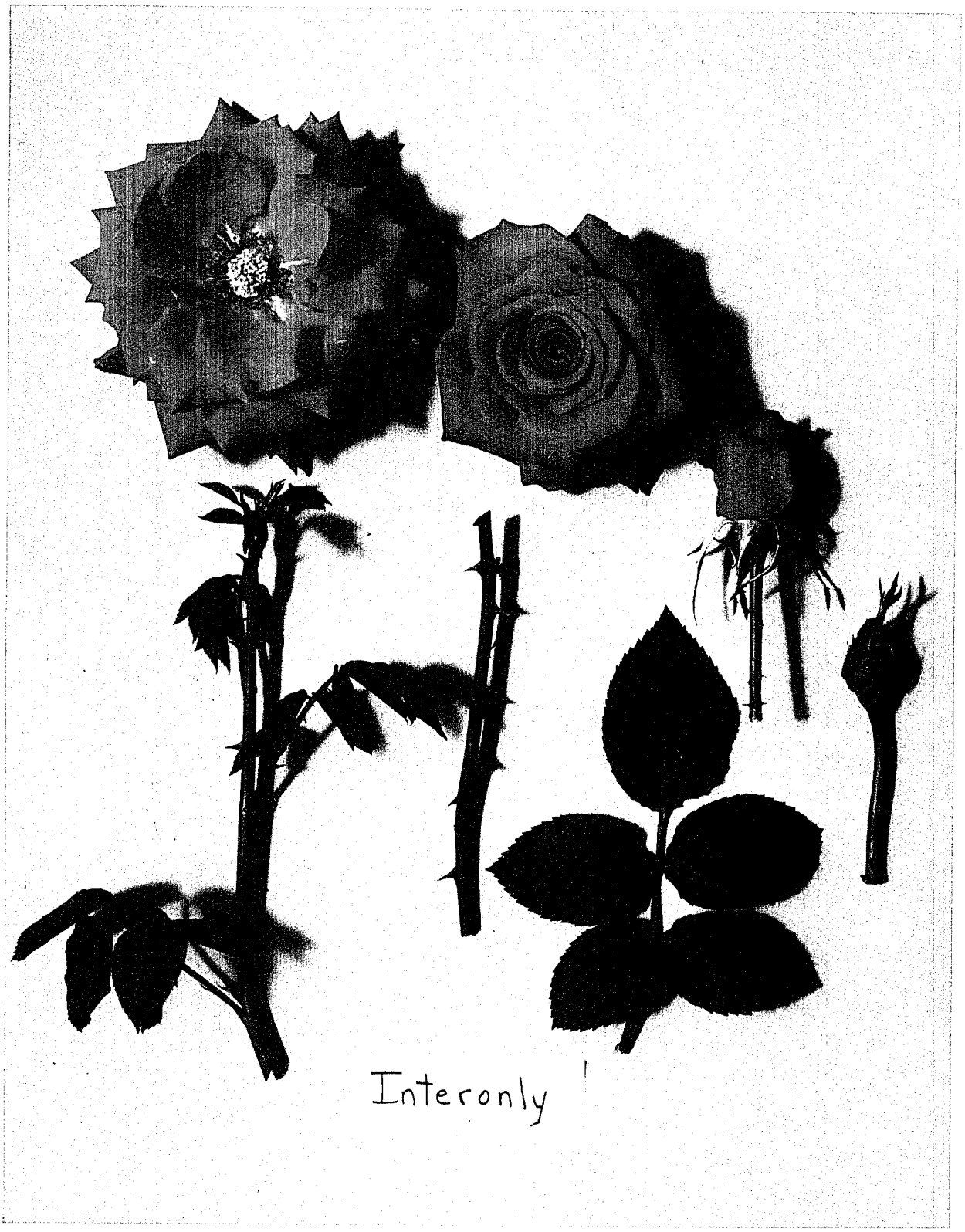
Interonly

UNITED STATES PATENT AND TRADEMARK OFFICE

CERTIFICATE OF CORRECTION

PATENT NO. : Plant 6,698

DATED : Mar. 28, 1989

INVENTOR(S) : Ilsink

It is certified that error appears in the above-identified patent and that said Letters Patent is hereby corrected as shown below:

Col. 2, line 44: "borwn" should be --brown--; and
Col. 4, line 26: "appended" should be --appendaged--.

Signed and Sealed this

Seventeenth Day of October, 1989

*Attest:*

DONALD J. QUIGG

*Attesting Officer*

*Commissioner of Patents and Trademarks*